United States Patent
Canut Jordana et al.

(10) Patent No.: US 12,037,643 B2
(45) Date of Patent: Jul. 16, 2024

(54) IN VITRO PHARMACOGENOMIC SCREENING METHOD FOR ANTICIPATING A PATIENT'S RESPONSE TO THE TREATMENT OF OCULAR HYPERTENSION

(71) Applicants: QUANTITATIVE GENOMIC MEDICINE LABORATORIES, S.L., Esplugues del Llobregat (ES); Maria Isabel Canut Jordana, Barcelona (ES); Ricardo Pedro Casaroli Marano, Barcelona (ES)

(72) Inventors: Maria Isabel Canut Jordana, Barcelona (ES); Ricardo Pedro Casaroli Marano, Barcelona (ES); Lluis Armengol Dulcet, Esplugues del Llobregat (ES); Olaya Villa Marcos, Esplugues del Llobregat (ES); Rafael Ignacio Barraquer Compte, Barcelona (ES)

(73) Assignee: Quantitative Genomic Medicine Laboratories, S.L., Barcelona (ES)

( * ) Notice: Subject to any disclaimer, the term of this patent is extended or adjusted under 35 U.S.C. 154(b) by 790 days.

(21) Appl. No.: 17/278,014

(22) PCT Filed: Sep. 13, 2019

(86) PCT No.: PCT/ES2019/070606
§ 371 (c)(1),
(2) Date: Mar. 19, 2021

(87) PCT Pub. No.: WO2020/058545
PCT Pub. Date: Mar. 26, 2020

(65) Prior Publication Data
US 2021/0381053 A1    Dec. 9, 2021

(30) Foreign Application Priority Data
Sep. 19, 2018  (EP) .................................. 18195545

(51) Int. Cl.
| | |
|---|---|
| *C12Q 1/6883* | (2018.01) |
| *A61K 31/5377* | (2006.01) |
| *A61K 31/5575* | (2006.01) |
| *A61P 27/02* | (2006.01) |

(52) U.S. Cl.
CPC ........ *C12Q 1/6883* (2013.01); *A61K 31/5377* (2013.01); *A61K 31/5575* (2013.01); *A61P 27/02* (2018.01); *C12Q 2600/106* (2013.01); *C12Q 2600/156* (2013.01)

(58) Field of Classification Search
None
See application file for complete search history.

(56) References Cited

U.S. PATENT DOCUMENTS

2009/0298839 A1    12/2009  McCarty

FOREIGN PATENT DOCUMENTS

| WO | WO 2011/004404 A1 | 1/2011 |
| WO | WO 2020/058545 A1 | 3/2020 |

OTHER PUBLICATIONS

Canut et al. Scientific Reports vol. 15(1583):9 pages, Jan. 15, 2021.*
Quigley, H.A., et al., The Number of People with Glaucoma Worldwide in 2010 And 2020, Br J Ophthalmol, vol. 90, No. 3, pp. 262-267, 2006.
Burdon et al., Genome-wide association study identifies susceptibility loci for open angle glaucoma at TMC01 and CDKN2B-AS1, Nature Genetics., vol. 43, No. 6, pp. 574-578, 2011.
Cheng et al., Focal Biologically Inspired Feature of Glaucoma Type Classification Medical image computing and computer-assisted intervention: MICCAI . . . International Conference of Medical Image Computing and Computer-Assisted Intervention, vol. 14, 2011.
Fan et al., Gene mapping for primary open angle glaucoma, Clinical Biochemistry, vol. 39, No. 3, dated Mar. 1, pp. 249-258, 2006.
Tezel, A proteomics view of the molecular mechanisms and biomarkers of glaucomatous neurodegeneration, Progress in Retinal and Eye Research, vol. 35, pp. 18-43, 2013.
Thorleifsson et al., Common variants near CAV1 and CAV2 are associated with primary open-angle glaucoma, Nature Genetics., vol. 42, No. 10, 10 pages, 2010.
Wiggs et al., Common Variants at 9p21 and 8q22 Are Associated with Increased Susceptibility to Optic Nerve Degeneration in Glaucoma, Plos Genetics, vol. 8, No. 4, 12 pages, 2012.
International Search Report and Written Opinion dated Dec. 12, 2019 in International Application No. PCT/ES2019/070606.

* cited by examiner

*Primary Examiner* — Sean McGarry
(74) *Attorney, Agent, or Firm* — Knobbe, Martens, Olson & Bear LLP

(57) ABSTRACT

In vitro pharmacogenomic screening method for anticipating a patient's response to the treatment of ocular hypertension
A method for in vitro screening a patient's response to the treatment of ocular hypertension involves obtaining a sample of a biological fluid from a patient, and determining the number of copies of an intronic portion of gene MLIP (MLIP-AS1). Detection of more than one copy of said MLIP-AS1 is an indication that the patient is a responder to a treatment with prostaglandins. Detection of less than one copy of MLIP-AS1 is an indication that the patient is a responder to a treatment with β-blockers.

6 Claims, No Drawings

IN VITRO PHARMACOGENOMIC SCREENING METHOD FOR ANTICIPATING A PATIENT'S RESPONSE TO THE TREATMENT OF OCULAR HYPERTENSION

PRIORITY AND CROSS REFERENCE TO RELATED APPLICATIONS

This application is the U.S. National Phase Application under 35 U.S.C. § 371 of International Application No. PCT/ES2019/070606, filed Sep. 13, 2019, designating the U.S. and published as WO 2020/058545 A1 on Mar. 26, 2020, which claims the benefit of European Application No. EP 18195545.1, filed Sep. 19, 2018. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to the field of in vitro screening.

BACKGROUND

Ocular hypertension means that the pressure of eyes, also known as intraocular hypertension (IOP), is higher than the pressure of healthy individuals. If left untreated, high eye pressure can cause glaucoma and permanent vision loss in some individuals.

SUMMARY

The present invention relates to a method to anticipate a patient's response to the treatment with the main drugs used for diseases involving ocular hypertension such as primary open-angle glaucoma (POAG).

DETAILED DESCRIPTION

There are several types of glaucoma, being the open-angle glaucoma (POAG) the most common. Glaucoma is a progressive neurodegenerative disease characterized by progressive degeneration of retinal ganglion cells. These are central nervous system neurons that have their cell bodies in the inner retina and axons in the optic nerve. Degeneration of these neurons results in cupping, a characteristic appearance of the optic disc and visual loss. The biological basis of glaucoma is poorly understood and the factors contributing to its progression have not been fully characterized. Glaucoma affects more than 70 million people worldwide with approximately 10% becoming bilaterally blind, making it the leading cause of irreversible blindness in the world (Quigley H A, Broman A T. The number of people with glaucoma worldwide in 2010 and 2020. Br J Ophthalmol. 2006;90(3):262-267). Glaucoma can remain asymptomatic until it is severe, resulting in a high likelihood that the number of affected individuals is much higher than the number known to have it.

The main protective element of retinal ganglion cells in hypertensive glaucoma is the reduction of IOP. IOP can be reduced in various ways. The treatment of choice to lower the ocular hypertension is mainly topical medication. At present, the most commonly used topical drugs are β-blockers and prostaglandins.

The administration of β-blocker drugs, which had been used to treat cardiovascular hypertension since the 1960s, was a breakthrough in glaucoma treatment since they significantly lowered IOP with fewer side effects than previous glaucoma drugs. Before the introduction of prostaglandin analogs, β-blockers were the most commonly prescribed treatment for glaucoma. In the late 1970s, a topical timolol maleate treatment became the first FDA approved β-blocker for the treatment of glaucoma. Timolol maleate is a non-selective β-blocker which decreases the formation of aqueous humor (AH) in the ciliary body.

Recently, a new family of drugs, the prostaglandin analogs, has become the first line of treatment. Naturally occurring prostaglandins bind a variety of cell surface receptors and are involved in mediating smooth muscle contraction and inflammation. Since their discovery, prostaglandins and their analogs have been studied as potential therapeutics in a number of diseases. Prostaglandin analogs have been shown to lower IOP mainly via increasing uveoscleral outflow, along with conventional AH outflow. While the specific mechanism of action of increasing outflow remains unknown, studies indicate that prostaglandin analogs affect extracellular matrix remodelling and may relax the ciliary body. Prostaglandin analogs have short half-lives and can be administered locally in the eye at low doses, which reduces the likelihood of side effects. The most commonly used prostaglandin in ophthalmology is latanoprost, which for example is the active ingredient of the medication sold under the brand name Xalatan®.

However, it is difficult to know a priori which one of the two above-mentioned drugs will be the best treatment for lowering ocular hypertension of a specific patient.

The inventors of the present invention have identified that there are two types of patients: responders and non-responders to the above-mentioned drug treatments; i.e., that the treatment response is not the same in each patient. Therefore, prior to starting topical treatment, there is a need of a screening tool that would help the specialists to anticipate the responder status of an individual, in order to select the appropriate drug treatment to lower ocular hypertension, thus avoiding a long-term treatment with insufficient or ineffective response and undesirable side effects.

To overcome the above-mentioned problems, the inventors of the present invention have discovered that the response of a patient to said drug treatments is related to the genetic profile of the patient. The determination of a specific genetic profile is a useful biomarker for anticipating the drug response of a patient. The inventors have found that variants in the MLIP gene can anticipate the response to a drug or the other.

In the present invention, the term "MLIP-AS1" is referred to a MLIP antisense RNA 1. MLIP is a Muscular-Enriched A-Type Laminin-Interacting Protein which to date, it is known to have a role in the growth and physiology of the heart and heart diseases.

Therefore, the present invention discloses an in vitro screening method to determine a patient's response to the treatment of ocular hypertension, comprising the steps of:
a) obtaining a sample of a biological fluid from a patient; and
b) determining the copy number of an intronic portion of the MLIP gene (MLIP-AS1);

wherein more than one copy of said MLIP-AS1 is an indication that the patient is better responder to the treatment with prostaglandins, and wherein less than one copy of said MLIP-AS1 is an indication that the patient is responder to the treatment with β-blockers.

In a particular embodiment, said β-blocker is timolol maleate.

In a particular embodiment, said prostaglandin is latanoprost.

On the other hand, said method is for the treatment of primary open-angle glaucoma (POAG).

In said method said biological fluid can be saliva, whole blood, plasma, serum, urine, among other biological fluids of a patient from which a genetic profile can be performed. Preferably, said biological fluid is saliva.

In said method, the number of copies of MLIP-AS1 is determined by any DNA analysis method known by the skilled person and suitable for such a quantification. For example multiplex ligation-dependent probe amplification (MLPA). In this case, an adhoc MLPA assay was developed to evaluate the individual number of copies. The MLPA mix included four control probes targeting copy-number neutral and non-variable regions plus probes targeting identified variable regions. Control DNA samples were also used in the procedure to normalize the values for each probe.

Hereinafter, the present invention is described with reference to one example, which however is not intended to limit the present invention.

EXAMPLES

Genetic profiles of response to the main drugs used in medical treatment of POAG and ocular hypertension.

Using array-based comparative genome hybridization (aCGH) technology, copy number differences at whole-genome level in responder and non-responder individuals to the different drug treatment were measured. This allowed to identify seven genomic regions (ranging in size between 3.8 and 46 Kb) that showed different copy number status (copy number variants termed 13q21, GSTT1, LCE1 D, PHACTR1, MLIP-AS1, 1p31 and 2q22) between the responding and non-responding groups of patients. The individual copy number of each of these seven candidate loci was validated by MLPA on each sample, with an MLPA probe designed specifically for each loci.

The following table shows the loci studied indicating the chromosome, the cytoband, the start and the end and the size.

| Locus | Chromosome | Cytoband | Start | End | Size |
|---|---|---|---|---|---|
| 1p31 | 1 | 1p31.1 | 72.766.555 | 72.801.950 | 35 Kb |
| LCE1D | 1 | 1q21.3 | 152.762.076 | 152.769.870 | 7.7 Kb |
| 2q22 | 2 | 2q22.3 | 146.865.725 | 146.876.364 | 10 Kb |
| PHACTR1 | 6 | 6p24.1 | 13.156.200 | 13.159.684 | 3.8 Kb |
| MLIP-AS1 | 6 | 6p12.1 | 53.929.240 | 53.934.834 | 5.5 Kb |
| 13q21 | 13 | 13q21.1 | 57.759.370 | 57.788.921 | 29 Kb |
| GSTT1 | 22 | 22q11.23 | 24.349.305 | 24.395.353 | 46 Kb |

Among the seven different loci, three exhibited statistically significant differences between responders and non-responders: 1p31 in the cohort of patients treated with β-blockers (BB), and MLIP-AS1 in the BB cohorts and in the cohort of patients treated with prostaglandins (PG).

MLIP-AS1 copy number showed differences between responders (n=52; x=0.22) and non-responders (n=40; x=0.43) (Fisher's exact test; p-val=0.0094) to β-blockers. The higher the number of copies of MLIP-AS1, the lower the capacity of β-blockers to diminish the intraocular pressure (OR=0.36; p-val=0.0025), thus having having 0 copies of MLIP-AS1 increases the odds of being a responder to β-blockers.

Similarly, distribution of MLIP copy number alleles was also significantly different between responders (n=57; x=0.395) and non-responders (n=47; x=0.191) to prostaglandin treatment (Fisher's exact test; p-val=0.0432). The presence of additional copies of MLIP-AS1 variant confers a significantly higher lowering capacity of intraocular pressure upon treatment with prostaglandins (OR=2.23, p-val=0.0148); thus, having 2 copies increases the odds of being a responder to prostaglandin treatment.

What is claimed is:
1. A method of treatment of ocular hypertension in a patient in need thereof, comprising:
   a) obtaining a sample of a biological fluid from the patient;
   b) determining the copy number of MLIP-AS1 gene in the patient's genome by analysing the sample; and
   (c) treating the patient with a prostaglandin if more than one copy of said MLIP-AS1 is present, or treating the patient with a 8-blocker if less than one copy of said MLIP-AS1 gene is present.
2. The method according to claim 1, wherein said 8-blocker is timolol maleate.
3. The method according to claim 1, wherein said prostaglandin is latanoprost.

4. The method according to claim 1, wherein said ocular hypertension is primary open-angle glaucoma (POAG).

5. The method according to claim 1, wherein said biological fluid is selected from the group consisting of saliva, whole blood, plasma, serum, and urine of the patient.

6. The method according to claim 5, wherein the biological fluid is saliva.

\* \* \* \* \*

UNITED STATES PATENT AND TRADEMARK OFFICE
CERTIFICATE OF CORRECTION

PATENT NO. : 12,037,643 B2
APPLICATION NO. : 17/278014
DATED : July 16, 2024
INVENTOR(S) : Maria Isabel Canut Jordana Page 1 of 1

It is certified that error appears in the above-identified patent and that said Letters Patent is hereby corrected as shown below:

On the Title Page

Column 2 (Abstract), Line 1-3, before "A method" delete "In vitro pharmacogenomic screening method for anticipating a patient's response to the treatment of ocular hypertension".

In the Claims

Column 4, Line 61, Claim 1, delete "8-blocker" and insert -- β-blocker --.

Column 4, Line 65, Claim 2, delete "8-blocker" and insert -- β-blocker --.

Signed and Sealed this
Eleventh Day of February, 2025

Coke Morgan Stewart
*Acting Director of the United States Patent and Trademark Office*